United States Patent
Tschirhart et al.

(10) Patent No.: US 10,078,779 B2
(45) Date of Patent: *Sep. 18, 2018

(54) GAZE TIME INDICATOR FOR A VEHICLE

(71) Applicant: VISTEON GLOBAL TECHNOLOGIES, INC., Van Buren Township, MI (US)

(72) Inventors: Michael Dean Tschirhart, Ann Arbor, MI (US); Dale O. Cramer, Royal Oak, MI (US); Anthony Joseph Ciatti, Ann Arbor, MI (US)

(73) Assignee: VISTEON GLOBAL TECHNOLOGIES, INC., Van Buren Township, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/443,594

(22) Filed: Feb. 27, 2017

(65) Prior Publication Data

US 2017/0190252 A1 Jul. 6, 2017

Related U.S. Application Data

(63) Continuation of application No. 13/911,969, filed on Jun. 6, 2013, now Pat. No. 9,619,695.

(51) Int. Cl.
| | |
|---|---|
| *B60K 28/06* | (2006.01) |
| *G06K 9/00* | (2006.01) |
| *G08B 21/06* | (2006.01) |
| *A61B 5/00* | (2006.01) |
| *G06F 3/01* | (2006.01) |
| *A61B 3/113* | (2006.01) |
| *B60W 50/14* | (2012.01) |

(Continued)

(52) U.S. Cl.
CPC ........ *G06K 9/00248* (2013.01); *B60K 28/066* (2013.01); *G08B 21/06* (2013.01); *A61B 3/113* (2013.01); *A61B 5/18* (2013.01); *A61B 5/6893* (2013.01); *A61B 5/746* (2013.01); *B60W 40/08* (2013.01); *B60W 50/14* (2013.01);
(Continued)

(58) Field of Classification Search
CPC ......... A61B 5/18; A61B 3/113; A61B 5/6893; A61B 5/746; G06K 9/00845; G06K 9/00597; B60K 28/066; B60K 2350/2013; B60W 50/14; B60W 40/08; B60W 2040/0818; B60W 2040/0836;
(Continued)

(56) References Cited

U.S. PATENT DOCUMENTS

| | | |
|---|---|---|
| 6,927,674 B2 | 8/2005 | Harter, Jr. et al. |
| 6,974,326 B2 | 12/2005 | Marple-Horvat |

(Continued)

*Primary Examiner* — Benyam Haile
(74) *Attorney, Agent, or Firm* — Klintworth & Rozenblat IP LLP

(57) ABSTRACT

A system for tracking a gaze of a driver of a vehicle includes a tracking device, a processor, a memory, and a display. The tracking device is configured to track a gaze of a driver of a vehicle. The processor is in electronic communication with the tracking device. The memory is in electronic communication with the processor. The memory includes programming code configured to be executed by the processor. The programming code is configured to determine in real-time a duration of the gaze of the driver of the vehicle tracked by the tracking device. The display is in electronic communication with the processor. The display is configured to display a symbol showing the determined duration, or a portion of the determined duration, of the gaze of the driver of the vehicle as determined by the processor.

24 Claims, 3 Drawing Sheets

(51) Int. Cl.
  *B60W 40/08* (2012.01)
  *G08B 21/04* (2006.01)
  *G06Q 40/08* (2012.01)
  *A61B 5/18* (2006.01)

(52) U.S. Cl.
  CPC .......... *G06F 3/013* (2013.01); *G06K 9/00597* (2013.01); *G06K 9/00845* (2013.01); *G06Q 40/08* (2013.01); *G08B 21/0476* (2013.01)

(58) Field of Classification Search
  CPC ..... B60W 2040/0845; B60W 2420/403; G06F 3/013; G08B 21/0476; G08B 21/02; G06Q 40/08
  See application file for complete search history.

(56) References Cited

U.S. PATENT DOCUMENTS

| | | | |
|---|---|---|---|
| 6,989,754 B2 | 1/2006 | Kisacanin et al. | |
| 7,565,230 B2 | 7/2009 | Gardner et al. | |
| 7,639,148 B2 * | 12/2009 | Victor | B60K 28/06 340/439 |
| 8,115,811 B2 | 2/2012 | Hiramaki | |
| 8,384,534 B2 | 2/2013 | James | |
| 2005/0030184 A1 | 2/2005 | Victor | |
| 2006/0190822 A1 | 8/2006 | Basson et al. | |
| 2008/0061958 A1 | 3/2008 | Birk | |
| 2010/0007479 A1 | 1/2010 | Smith | |
| 2011/0169525 A1 | 7/2011 | James | |
| 2012/0092173 A1 | 4/2012 | Sanchez | |
| 2012/0200490 A1 | 8/2012 | Inada | |
| 2012/0215403 A1 | 8/2012 | Tengler et al. | |
| 2012/0268262 A1 | 10/2012 | Popovic | |
| 2013/0058529 A1 | 3/2013 | Levin | |
| 2014/0160011 A1 | 6/2014 | Park | |
| 2014/0168399 A1 * | 6/2014 | Plummer | B60Q 9/00 348/78 |
| 2014/0172467 A1 | 6/2014 | He | |
| 2014/0210978 A1 | 7/2014 | Gunaratne | |

* cited by examiner

GAZE TIME INDICATOR FOR A VEHICLE

CROSS-REFERENCE TO RELATED APPLICATION

This application is a continuation of U.S. patent application Ser. No. 13/911,969, filed Jun. 6, 2013, the contents of which are herein incorporated by reference in their entirety.

FIELD OF THE DISCLOSURE

This disclosure relates to a system and method for tracking a gaze of a driver of a vehicle and provides the driver with feedback regarding the tracked gaze of the driver.

BACKGROUND

Drivers of vehicles often incur distractions while driving. These distractions can include the driver looking away from the path of travel to view objects within or outside the vehicle such as other people, animals, a vehicle console, a vehicle instrument, a phone, or another type of object. This can be unsafe and can increase the likelihood of an accident. Drivers are typically poorly calibrated to the duration and consequent implications of their gaze on objects other than the road. Systems exist for monitoring a gaze of a driver of a vehicle and when improper gazing occurs doing one of: issuing a visual or auditory warning to the driver; disabling a vehicle system being improperly viewed; automatically taking corrective action; shutting down the vehicle if improper viewing continues; or taking other types of corrective action. However, the driver may shut down such monitoring systems because they may become a nuisance to the driver.

A system and method is needed to alert a driver of a vehicle of the driver's improper viewing of objects other than the path of travel of the vehicle without becoming an undue nuisance to the driver.

SUMMARY

In one embodiment, a system for tracking a gaze of a driver of a vehicle is disclosed. The system may include a tracking device, a processor, a memory, and a display. The tracking device is configured to track a gaze of a driver of a vehicle. The processor is in electronic communication with the tracking device. The memory is in electronic communication with the processor. The memory includes programming code configured to be executed by the processor. The programming code is configured to determine in real-time a duration of the gaze of the driver of the vehicle tracked by the tracking device. The display is in electronic communication with the processor. The display is configured to display a symbol showing the determined duration, or a portion of the determined duration, of the gaze of the driver of the vehicle as determined by the processor.

In another embodiment, a vehicle for tracking a gaze of a driver of the vehicle is disclosed. The vehicle includes a tracking device, a processor, a memory, and a display. The tracking device is configured to track a gaze of a driver of the vehicle. The processor is in electronic communication with the tracking device. The memory is in electronic communication with the processor. The memory includes programming code configured to be executed by the processor. The programming code is configured to determine in real-time a duration of the gaze of the driver of the vehicle tracked by the tracking device. The duration is how much time the driver has been continuously gazing at one or more objects other than a path in which the vehicle is moving. The display is in electronic communication with the processor. The display is configured to display a symbol showing the determined duration, or a portion of the determined duration, of the gaze of the driver of the vehicle as determined by the processor.

In still another embodiment, a method of tracking a gaze of a driver of a vehicle is disclosed. In one step, a gaze of a driver of a vehicle is tracked with a tracking device. In another step, a duration of the gaze of the driver of the vehicle, as tracked by the tracking device, is determined in real-time by a processor. In yet another step, a symbol is displayed on a display showing the determined duration, or a portion of the determined duration, of the gaze of the driver of the vehicle tracked by the tracking device as determined by the processor.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
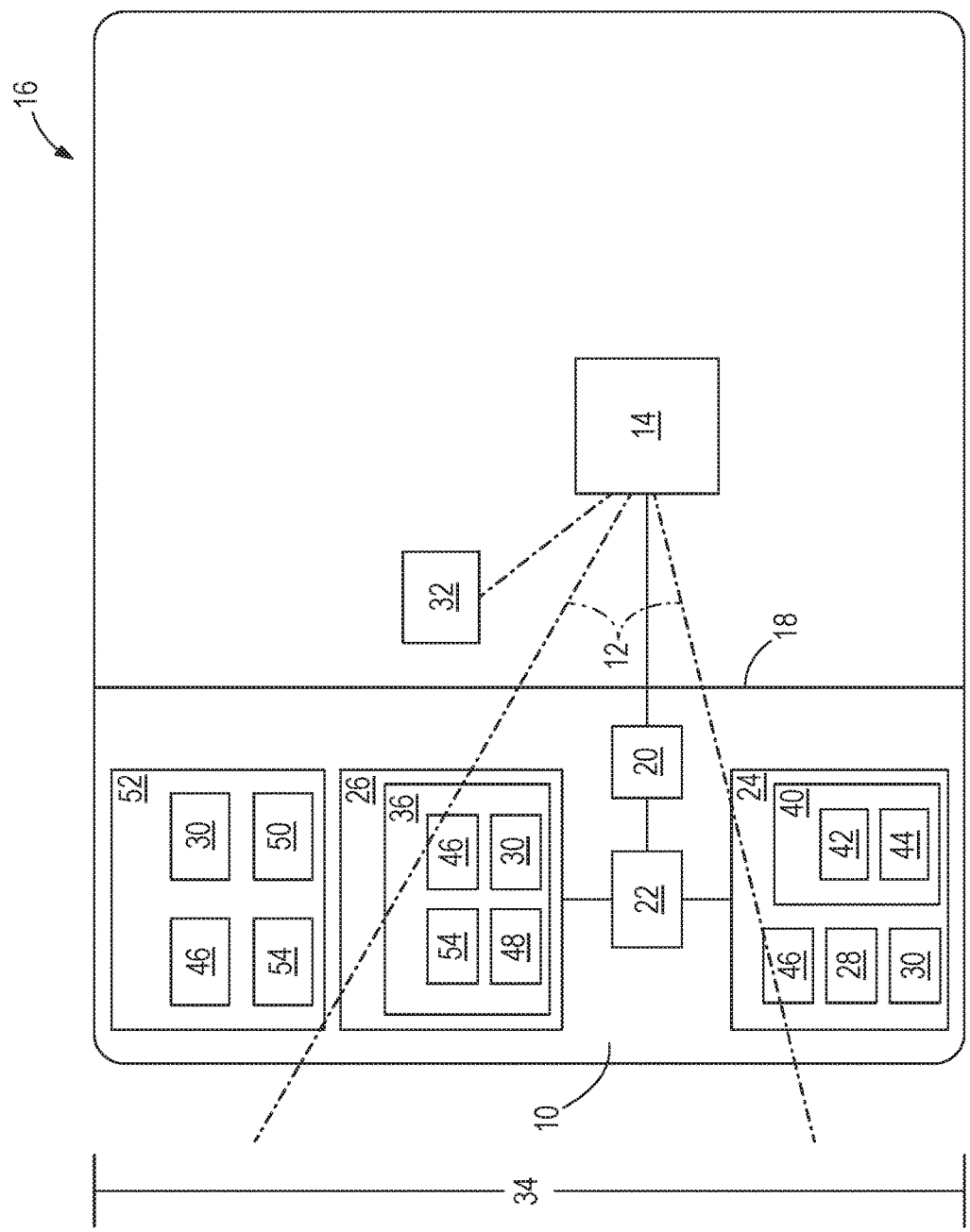
FIG. 1 illustrates a box diagram of one embodiment of a system for tracking a gaze of a driver of a vehicle.

FIG. 1 illustrates a box diagram of one embodiment of a system 10 for tracking a gaze 12 of a driver 14 of a vehicle 16. The system 10 may be installed in the vehicle 16. The system 10 may comprise a portion 18 of the vehicle 16. The portion 18 of the vehicle 16 may comprise a vehicle console, a vehicle instrument, or another portion of the vehicle 16. The vehicle 16 may comprise an automobile, a submarine, a boat, a train, a military vehicle, a plane, a spaceship, or another type of vehicle. The system 10 may include a tracking device 20, a processor 22, a memory 24, and a display 26. In other embodiments, the system 10 may contain varying components. The tracking device 20 is configured to track the gaze 12 (such as the angle of the driver's gaze) of the driver 14 of the vehicle 16 to determine what the driver is looking at. The tracking device 20 may comprise an eye tracking device, a head tracking device, or another type of tracking device for tracking the driver's gaze to determine what the driver is looking at. The processor 22 is in electronic communication with the tracking device 20. The memory 24 is in electronic communication with the processor 22. The memory 24 contains programming code 28 configured to be executed by the processor 22.

The programming code 28 is configured to determine in real-time a duration 30 of the gaze 12 of the driver 14 of the vehicle 16 as tracked by the tracking device 20. In one embodiment, the duration 30 comprises how much time the driver 14 has been continuously gazing at one or more objects 32 other than at a path 34 in which the vehicle 16 is moving. The path 34 in which the vehicle 16 is moving may comprise a road, a water path, a flight path, a space path, a rail path, or another type of path in which the vehicle 16 is moving. The one or more objects 32 may comprise an instrument of the vehicle 16, a console of the vehicle 16, a person in the vehicle 16, an animal in the vehicle 16, an object in the vehicle 16, an object outside of the vehicle 16, or another type of object other than the path 34 in which the vehicle 16 is moving. In another embodiment, the duration 30 comprises how much time the driver 14 has been continuously gazing, while the vehicle 16 is continuously moving, at the one or more objects 32 other than the path 34 in which the vehicle 16 is moving. In still another embodiment, the programming code 28 may be configured to reset the determined duration 30 when the driver 14 switches from gazing at the one or more objects 32 to gazing at the path 34 in which the vehicle 16 is moving or when the vehicle 16 stops moving. In other embodiments, what determines the duration 30 may vary, and the programming code 28 may be configured to reset the determined duration 30 as a result of varying occurrences.

The display 26 is in electronic communication with the processor 22. The display 26 is configured to display a symbol 36 showing the determined duration 30, or a portion of the determined duration 30, of the gaze 12 of the driver 14 of the vehicle 16 as determined by the processor 22. The symbol 36 may comprise a graph, a bar indicator, a pie chart, a number, a word, or another type of symbol showing the determined duration 30, or a portion of the determined duration 30, of the gaze 12 of the driver 14 of the vehicle 16 as determined by the processor 22. The memory 24 may be configured to store all duration 30 determinations of the processor 22 for viewing on the display 26 at any time. The memory 24 may store a database 40. The database 40 may contain location coordinates 42 of the one or more objects 32 or may contain location coordinates 42 of the path 34 in which the vehicle 16 is moving. The database 40 may further contain identifications 44 of the one or more objects 32 with their respective corresponding location coordinates 42. In other embodiments, the memory 24 may store varying items of information, and the database 40 may also contain varying information.

The programming code 28 may be further configured to determine whether the duration 30 of the gaze 12 of the driver 14 of the vehicle 16 exceeds a threshold 46 and if it does to display a visual warning 48 on the display 26 or to sound an audio warning 50 through an audio device 52 of the system 10. The threshold 46 may comprise a determined safe duration, which is pre-determined or determined in real-time by the processor 22, for the driver 14 of the vehicle 16 to be viewing the one or more objects 32 while driving the vehicle 16. For instance, in one embodiment the threshold 46 may comprise a two second safe duration for a driver to be viewing the one or more objects 32 while driving the vehicle 16. In other embodiments, the threshold 46 may vary. The programming code 28 may be additionally configured to: display the full duration 30 or a portion of the duration 30 of the gaze 12 of the driver 14 on the display 26; display the threshold 46 on the display 26; to display on the display 26 a difference 54 between the duration 30 of the gaze 12 and the threshold 46; to sound the audio warning 50 through the audio device 52 stating the duration 30; to sound the audio warning 50 through the audio device 52 stating the threshold 46; or to sound the audio warning 50 through the audio device 52 stating the difference 54 between the duration 30 of the gaze 12 and the threshold 46. In other embodiments, the programming code 28 may be configured to do additional activities to alert the driver 14 of the vehicle 16 of the determined duration 30, to alert the driver 14 of the threshold 46, or to alert the driver 14 that the determined duration 30 has exceeded the threshold 46. In still additional embodiments, the programming code 28 may be programmed to do still other functions.

Figure 2:
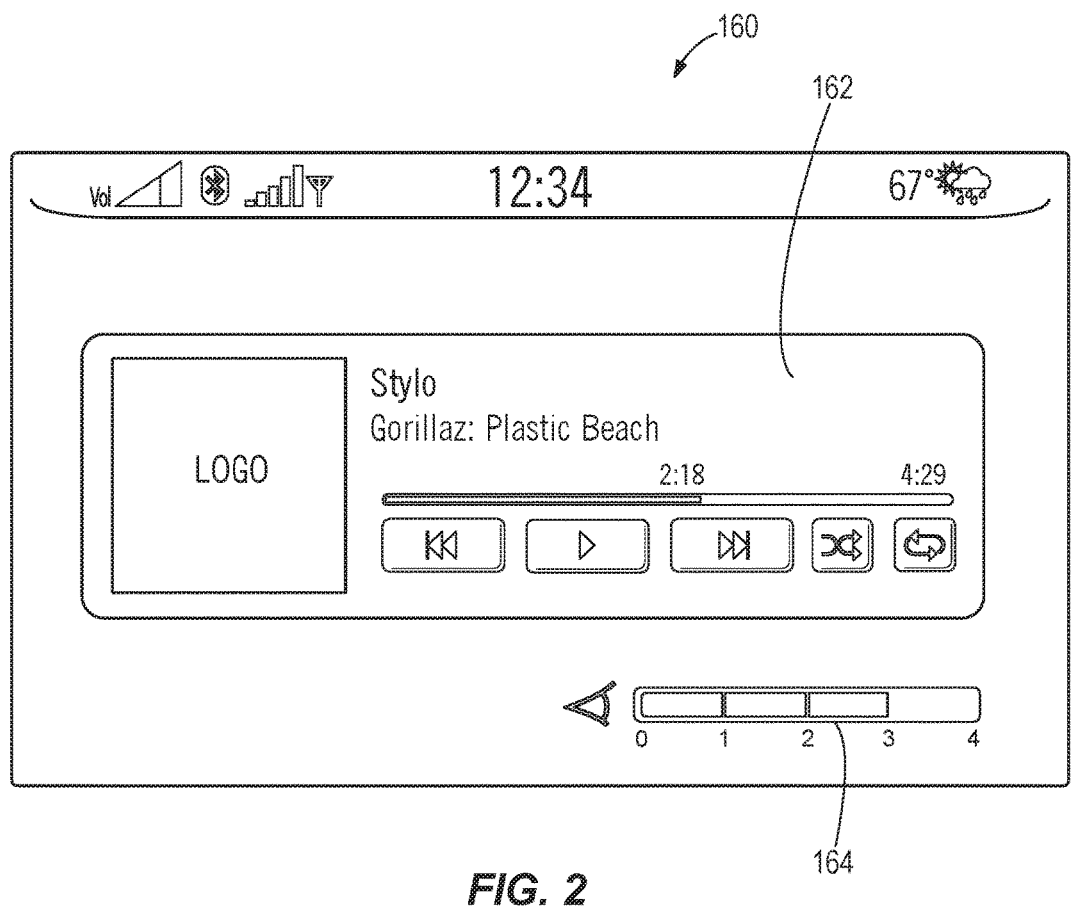
FIG. 2 illustrates a front view of one embodiment of a vehicle instrument display utilizing the system of FIG. 1.

FIG. 2 illustrates a front view of one embodiment of a vehicle instrument display 160 utilizing the system 10 of FIG. 1. The vehicle instrument display 160 comprises a music control 162 and a symbol 164. The music control 162 allows the driver of the vehicle to control the music being played in the vehicle. The symbol 164 comprises a bar indicator showing the determined duration, or a portion of the determined duration, of the gaze of the driver when the driver is looking at objects other than the path on which the vehicle is traveling. In one embodiment in which the threshold is two seconds (i.e. the period of time deemed to be safe for a driver to be looking at objects other than the path on which the vehicle is traveling), the bar indicator may begin filling up to track the duration the driver has been looking at the music control 162. When the driver has been looking at the music control 162 for one-and-a-half seconds the bar indicator may turn colors, flash, or otherwise graphically alert the driver that the threshold is being approached. An audio alarm may also go off. When the threshold is met or exceeded, the bar indicator may further turn colors, flash, or otherwise graphically alert the driver that the threshold has been met or exceeded. In other embodiments, the vehicle instrument display may vary, the threshold may vary, the symbol may vary, the symbol may only show a portion of the driver's gaze duration (i.e. for instance the symbol may only start showing the driver's gaze when the driver's gaze is within a set time difference away from the threshold such as only starting to show the driver's gaze when it has reached one-and-a-half seconds when the threshold is two seconds; or the symbol may only start showing the driver's gaze when the driver's gaze has reached the threshold such as two seconds), or other items may be varied.

Figure 3:
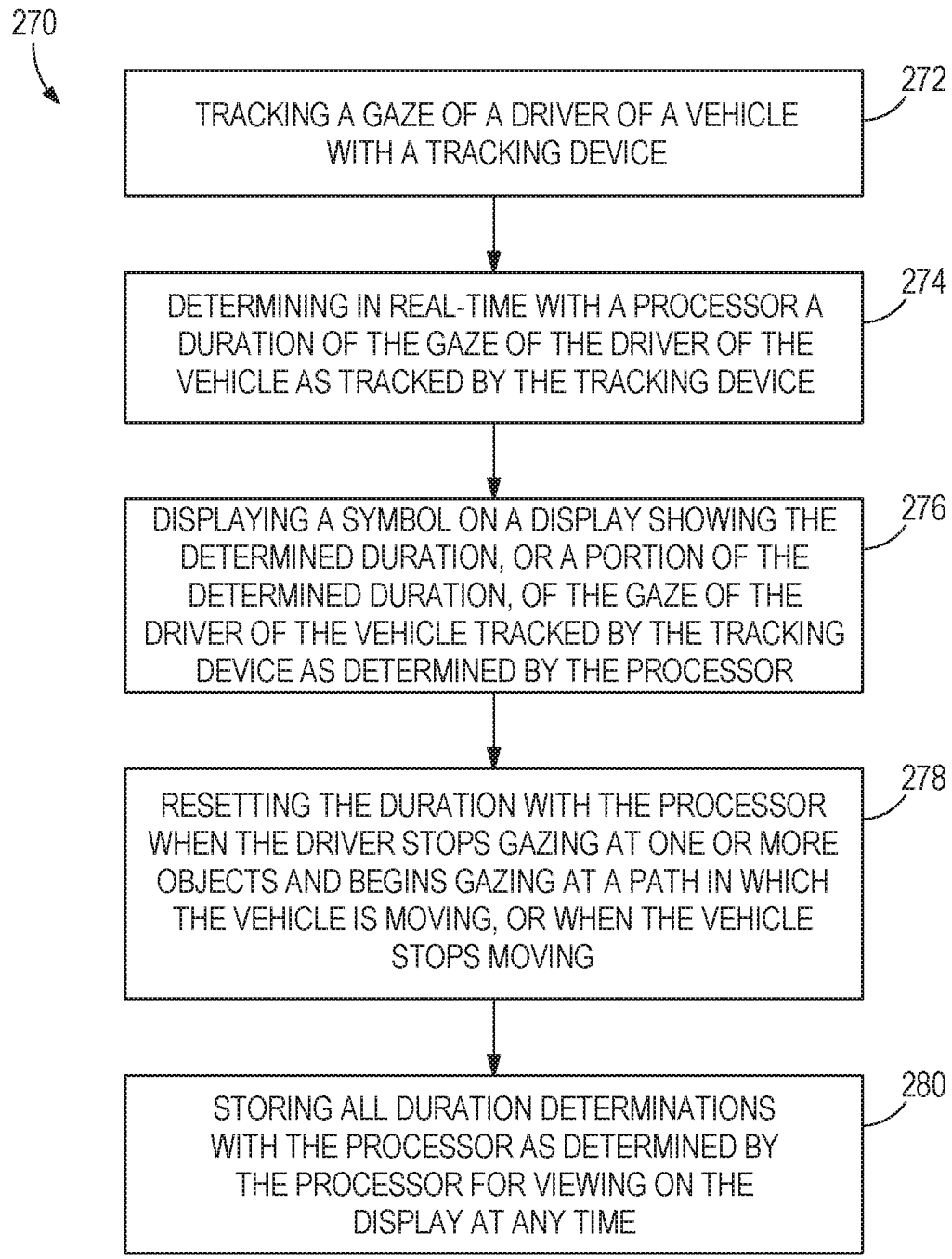
FIG. 3 is a flowchart illustrating one embodiment of a method of tracking a gaze of a driver of a vehicle.

FIG. 3 is a flowchart illustrating one embodiment of a method 270 of tracking a gaze of a driver of a vehicle. The method 270 may utilize any of the embodiments disclosed herein including the system 10 disclosed in FIG. 1 and the vehicle instrument display 160 disclosed in FIG. 2. In step 272, a gaze (such as an angle of the driver's gaze) of a driver of a vehicle is tracked with a tracking device to determine what object the driver is looking at. The tracking device may comprise an eye gaze tracking device, a head gaze tracking device, or another type of tracking device for determining the driver's gaze to determine what the driver is looking at. In step 274, a processor determines in real-time a duration of the gaze of the driver of the vehicle as tracked by the tracking device. The duration may comprise how much time the driver has been continuously gazing at one or more objects other than a path in which the vehicle is moving. The path in which the vehicle is moving may comprise a road, a water path, a flight path, a space path, a rail path, or another type of path in which the vehicle is moving. The one or more objects may comprise an instrument of the vehicle, a console of the vehicle, a person in the vehicle, an animal in the vehicle, an object in the vehicle, an object outside of the vehicle, or another type of object. In one embodiment, the processor may only determine the duration while the vehicle is moving. In one embodiment, step 274 may further comprise the processor determining location coordinates of the one or more objects or determining location coordinates of the path in which the vehicle is moving. In yet another embodiment, step 274 may additionally comprise the processor determining an identification of the one or more objects based on the determined location coordinates.

In step 276, a symbol is displayed on a display showing the determined duration, or a portion of the determined duration, of the gaze of the driver of the vehicle tracked by the tracking device as determined by the processor. The display may comprise a portion of a console of the vehicle or another type of display. The symbol may comprise a graph, a bar indicator, a pie chart, a number, a word, or another type of symbol. In another embodiment, step 276 may further comprise the processor determining whether the duration of the gaze exceeds a threshold and if it does the processor displaying a visual warning on the display or sounding an audio warning through an audio device of the vehicle. In another embodiment, step 276 may further comprise the processor: displaying the full duration or displaying a portion of the duration of the gaze of the driver on the display; displaying the threshold on the display; displaying on the display a difference between the duration of the gaze and the threshold; sounding the audio warning through the audio device of the vehicle stating the duration; sounding the audio warning through the audio device of the vehicle stating the threshold; sounding the audio warning through the audio device of the vehicle stating the difference between the duration of the gaze and the threshold; or doing varying functions.

In step 278, the processor may reset the duration when the driver stops gazing at the one or more objects and begins gazing at the path in which the vehicle is moving, or when the vehicle stops moving. In step 280, the processor may store all duration determinations as determined by the processor for viewing on the display at any time. This may assist the driver in determining how well or poorly he or she has been driving the vehicle in order to change the driver's driving habits if they are dangerous. In other embodiments, one or more steps of the method 160 may vary in substance or order, may not be followed, or one or more additional steps may be added.

One or more embodiments of the disclosure may provide passive feedback regarding driver cognitive state to a driver of a vehicle. Such a system may passively alert the driver of his or her improper viewing of objects other than a path of travel of the vehicle without changing a function of the vehicle. This type of system may lead to an increase in the probability that the driver will utilize the safety system as the driver is less likely to view it as a nuisance. Usage of such a system may increase the driver's safety while driving, and may decrease the likelihood of an accident.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A system for tracking a gaze of a driver of a vehicle comprising:
   a tracking device configured to track a gaze of a driver of a vehicle;
   a processor in electronic communication with the tracking device;
   a memory in electronic communication with the processor, the memory comprising programming code configured to be executed by the processor, the programming code configured to determine in real-time a duration of the gaze of the driver of the vehicle away from a path in which the vehicle is moving, and further configured to determine an object that the driver of the vehicle is viewing outside the vehicle and to passively alert the driver of his improper viewing of the object other than the path; and
   a display in electronic communication with the processor, the display configured to, as controlled by the processor, display an indicator which in real-time fills up, while the vehicle is moving and the driver of the vehicle is gazing away from the path in which the vehicle is moving, to track and display the real-time determined duration of the gaze of the driver as determined by the processor.

2. The system of claim 1 wherein the programming code is further configured to determine in real-time whether the duration exceeds a threshold of safe duration away from the path in which the vehicle is moving.

3. The system of claim 2 wherein the programming code is further configured to cause the system to alert the driver when the duration meets or exceeds said threshold.

4. The system of claim 2 wherein the programming code is further configured to cause the display to display the threshold.

5. The system of claim 1 wherein the system is configured to passively update the driver regarding the duration without changing a function of the vehicle.

6. The system of claim 1 wherein the programming code is further configured to reset the duration when the vehicle stops moving.

7. The system of claim 6 wherein the programming code is further configured to cause the memory to store all duration determinations of the processor for later viewing on the display.

8. The system of claim 2 wherein the programming code is further configured to cause the display to display a difference between the duration and the threshold.

9. The system of claim 2 further comprising an audio device, the programming code further configured to cause the audio device to state the duration or the threshold.

10. The system of claim 2 further comprising an audio device, the programming code further configured to cause the audio device to state the difference between the duration and the threshold.

11. A method of tracking a gaze of a driver of a vehicle comprising:
    tracking a gaze of a driver of a vehicle with a tracking device;

determining in real-time, with a processor, a duration of the gaze of the driver of the vehicle away from a path in which the vehicle is moving, and further determining in real-time, with the processor, an object that the driver is viewing outside the vehicle and passively alerting the driver of his improper viewing of the object other than the path in which the vehicle is moving; and displaying an indicator on a display which in real-time fills up, while the vehicle is moving and the driver of the vehicle is gazing away from the path in which the vehicle is moving, to track and display the real-time determined duration of the gaze of the driver of the vehicle tracked by the tracking device as determined by the processor.

12. The method of claim 11 further comprising the processor determining in real-time whether the duration exceeds a threshold of safe duration away from the path in which the vehicle is moving.

13. The method of claim 12 further comprising the processor causing the driver to be alerted when the duration meets or exceeds said threshold.

14. The method of claim 12 further comprising the processor causing the display to display the threshold.

15. The method of claim 11 further comprising the processor causing the driver to be passively updated regarding the duration without changing a function of the vehicle.

16. The method of claim 11 further comprising the processor resetting the duration when the vehicle stops moving.

17. The method of claim 16 further comprising the processor causing a memory to store all duration determinations of the processor for later viewing on the display.

18. The method of claim 12 further comprising the processor causing the display to display a difference between the duration and the threshold.

19. The method of claim 12 further comprising the processor causing an audio device to state the duration or the threshold.

20. The method of claim 12 further comprising the processor causing an audio device to state the difference between the duration and the threshold.

21. The system of claim 1 wherein the indicator is a bar indicator.

22. The system of claim 1 wherein the programming code is further configured to cause the system to alert the driver when the duration is approaching a threshold of safe duration away from the path in which the vehicle is moving.

23. The system of claim 22 wherein the programming code is further configured to cause the indicator to turn colors or flash when the duration is approaching the threshold of safe duration away from the path in which the vehicle is moving.

24. The system of claim 3 wherein the programming code is further configured to cause the indicator to turn colors or flash when the duration meets or exceeds the threshold of safe duration away from the path in which the vehicle is moving.

* * * * *